United States Patent
Kjellstrom et al.

(10) Patent No.: US 8,594,790 B2
(45) Date of Patent: Nov. 26, 2013

(54) SYSTEM AND METHOD FOR MONITORING A VENTRICULAR PRESSURE INDEX TO PREDICT WORSENING HEART FAILURE

(75) Inventors: Barbro M. Kjellstrom, Minneapolis, MN (US); Tommy D. Bennett, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 1644 days.

(21) Appl. No.: 11/045,571

(22) Filed: Jan. 27, 2005

(65) Prior Publication Data
US 2006/0167516 A1 Jul. 27, 2006

(51) Int. Cl.
*A61N 1/365* (2006.01)
*A61B 5/021* (2006.01)

(52) U.S. Cl.
USPC ............................. 607/23; 600/485

(58) Field of Classification Search
USPC ............................. 600/485; 607/23
See application file for complete search history.

(56) References Cited

U.S. PATENT DOCUMENTS

| | | | |
|---|---|---|---|
| 5,163,429 A | 11/1992 | Cohen | |
| 5,368,040 A | 11/1994 | Carney | |
| 5,564,434 A | 10/1996 | Halperin et al. | |
| 5,758,652 A * | 6/1998 | Nikolic | 600/487 |
| 5,904,708 A | 5/1999 | Goedeke | |
| 6,314,323 B1 | 11/2001 | Ekwall | |
| 6,865,419 B2 * | 3/2005 | Mulligan et al. | 607/23 |
| 2002/0120201 A1 * | 8/2002 | Chio et al. | 600/490 |
| 2003/0055461 A1 | 3/2003 | Girouard et al. | |
| 2003/0093125 A1 | 5/2003 | Zhu et al. | |
| 2003/0199813 A1 * | 10/2003 | Struble | 604/66 |
| 2004/0167580 A1 | 8/2004 | Mann et al. | |

OTHER PUBLICATIONS

"Notification Concerning Transmittal of International Preliminary Report on Patentability (Chapter I of the Patent Cooperation Treaty)" for related application PCT/US2006/002954, dated Aug. 9, 2007.

* cited by examiner

*Primary Examiner* — Tammie K Heller
(74) *Attorney, Agent, or Firm* — Reed A. Duthler; Stephen W. Bauer

(57) ABSTRACT

A medical device monitors a patient to predict worsening heart failure. An input circuit of the medical device receives a pressure signal representative of a pressure sensed within a ventricle of the patient's heart as a function of time. A processor derives from the pressure signal a ventricular pressure index for a ventricular contraction based upon pressures in the ventricle. The processor then provides an output based upon the ventricular pressure index.

19 Claims, 5 Drawing Sheets

US 8,594,790 B2

SYSTEM AND METHOD FOR MONITORING A VENTRICULAR PRESSURE INDEX TO PREDICT WORSENING HEART FAILURE

BACKGROUND OF THE INVENTION

The present invention relates generally to cardiac monitoring, and more particularly, to the monitoring of cardiac pressures in a patient's heart to detect worsening heart failure.

Heart failure is a chronic condition for which there is no cure, but which can be slowed with early diagnosis and ongoing treatment to improve an individual's quality of life. Heart failure is the result of a weakened heart muscle that can no longer efficiently pump blood to meet the demands of the body. With heart failure, circulation is impaired and blood pressure increases in the heart.

For certain patients, it may be beneficial to chronically monitor various hemodynamic parameters in the patient's heart in an outpatient setting to detect worsening heart failure, thus allowing the physicians to adjust the patient's therapies to decrease the disease's progression and thus decrease the risk of death and the need for hospitalization. One device that allows such hemodynamic monitoring is the MEDTRONIC CHRONICLE Model 9520 Implantable Hemodynamic Monitor (IHM), which, when coupled with a pressure sensor located in the right ventricle of the heart, can be programmed to measure and record over time right ventricle (RV) systolic pressure, RV diastolic pressure, pulse pressure, pre-ejection interval (PEI), systolic time interval (STI), peak positive and negative dP/dt, estimated pulmonary artery diastolic pressure (ePAD), patient activity level, and heart rate.

Although the tracking of these individual hemodynamic parameters has proven helpful in treating patients, there remains a need for further indicators of worsening heart failure.

BRIEF SUMMARY OF THE INVENTION

The present invention is based upon the discovery that a ventricular pressure index for a ventricular contraction, which is based upon pressures in the ventricle, is a predictor of worsening heart failure. The present invention includes a medical device and methods for determining and using the ventricular pressure index.

The medical device monitors heart failure in a patient and includes an input circuit and a processor. The input circuit receives a pressure signal representative of a pressure sensed within a ventricle of the patient's heart as a function of time. The processor derives from the pressure signal a ventricular pressure index for a ventricular contraction based upon pressures in the ventricle. The processor then provides an output based upon the ventricular pressure index.

A method for predicting worsening heart failure in a heart failure patient begins by sensing a blood pressure within a ventricle of the patient's heart as a function of time. From these sensed blood pressures, a ventricular pressure index for a ventricular contraction is derived based upon blood pressures in the ventricle. An output based upon the ventricular pressure index is provided.

A method for determining an optimal set of pacing settings for a pacemaker implanted in a patient with heart failure begins by administering a plurality of pacing settings. Each pacing setting is administered for a period of time. An effect of each pacing setting on a ventricular pressure index is then monitored. The ventricular pressure index is determined from a pressure signal sensed from within a ventricle of the patient's heart. Finally, a set of pacing settings is selected from the plurality of pacing settings based upon the ventricular pressure index.

DETAILED DESCRIPTION

Figure 1:
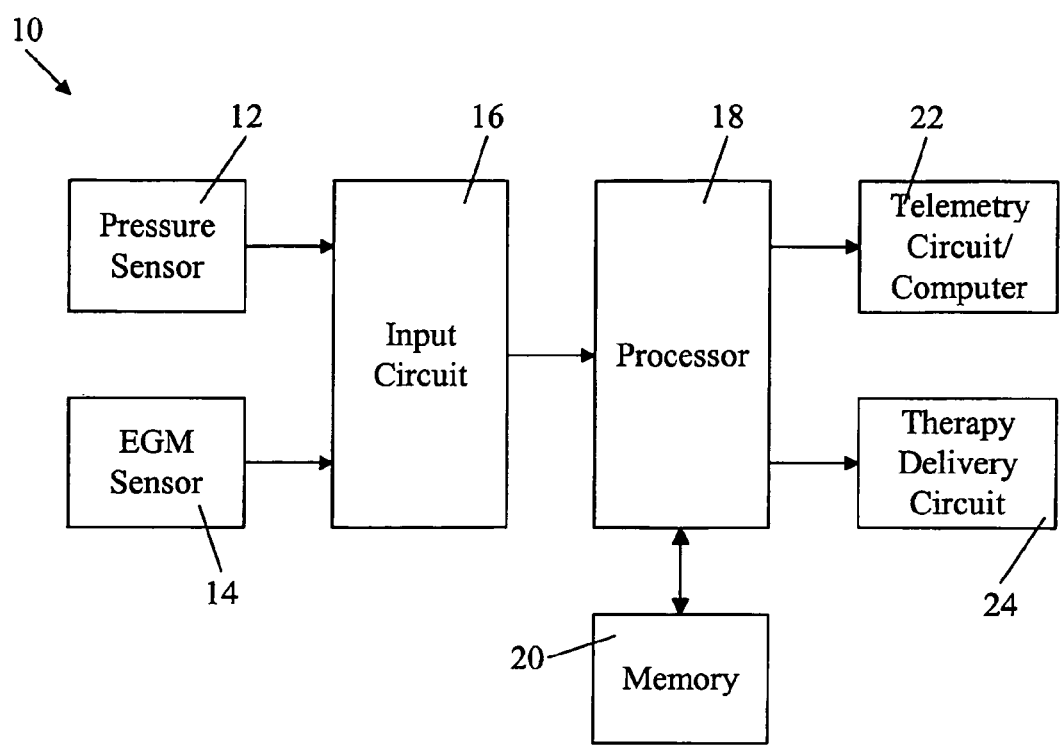
FIG. 1 is a block diagram of a system in accord with the present invention for monitoring heart failure in a patient using the ventricular pressure index.

FIG. 1 is a block diagram of system 10 for monitoring heart failure in a patient. System 10 includes pressure sensor 12, electrogram (EGM) sensor 14, input circuit 16, processor 18, memory 20, telemetry circuit/computer 22, and therapy delivery circuit 24. Pressure sensor 12 is located inside the patient's heart to sense blood pressures therein. EGM sensor 14 is an electrode located to sense the electrical activity of the heart. For example, both pressure sensor 12 and EGM sensor 14 may be positioned in a ventricle of the heart (typically the right ventricle).

Input circuit 16 is a signal processing circuit that receives a pressure signal representative of blood pressures in the ventricle as a function of time from pressure sensor 12 and an electrical signal representative of the electrical activity in the heart as a function of time from EGM sensor 14. Input circuit 16 may sample, demodulate or otherwise process the signals received from pressure sensor 10 and electrode sensor 12.

From these processed pressure and electrical signals received from input circuit 16, processor 18 derives several hemodynamic parameters defining the pressures in the ventricle, including the systolic pressure, the diastolic pressure, and the pulse pressure. Processor 18 also estimates a diastolic pressure in the blood vessel into which the ventricle pumps blood. Where an additional pressure sensor is located in the blood vessel, an exact measure of the diastolic pressure in the blood vessel may replace the estimate. These hemodynamic parameters are then stored in memory 20 by processor 18 on a beat-by-beat basis, minute-to-minute basis, hour-to-hour basis, or on some other basis.

Processor 18 next uses these hemodynamic parameters to further derive an ventricular pressure index (VPI) as follows:

$$VPI = VPP - eBV_{dias} = (VP_{sys} - VP_{dias}) - eBV_{dias}$$

where VPP is the ventricular pulse pressure, $eBV_{dias}$ is the diastolic pressure in the blood vessel, $VP_{sys}$ is the systolic pressure in the ventricle, and $VP_{dias}$ is the diastolic pressure in the ventricle.

In some embodiments of the present invention, processor 18 next compares the ventricular pressure index to the patient's ventricular pressure index threshold stored in memory 20. The patient's ventricular pressure index threshold may be determined during an initializing period in which the patient is monitored to establish a baseline, or normal, value for his/her ventricular pressure index. The threshold can then be set as a value less than the baseline, for example, a value 5%-50% less than the baseline value.

Any decreases in the ventricular pressure index below the threshold is a predictor of diminished ventricular performance and/or worsening heart failure status such that additional medical intervention may be warranted. Thus, in one embodiment, processor 18 instructs telemetry circuit 22 to transmit an alert to medical personnel whenever the ventricular pressure index falls below the ventricular pressure index threshold. Alternately, telemetry circuit 22 may be replaced with a local computer terminal with the capability to display the alert for medical personnel. Telemetry circuit/computer 22 also allows a user, such as the medical personnel, to exchange information, including sensed data and programming parameters, with processor 18.

In other embodiments, processor 18, upon the detection of the ventricular pressure index falling below the ventricular pressure index threshold, may automatically provide a therapy control signal to therapy delivery circuit 24 to adjust or titrate any of various therapies being administered to the patient.

In still other embodiments, a patient, after "crashing, may have her ventricular pressure index monitored to evaluate her response to treatment, with an increase in her ventricular pressure index indicative of a positive response to the treatment.

The derivation of the ventricular pressure index may also be useful in the optimization of a patient's pacemaker settings. In particular, a set of pacing settings can be initially selected or subsequently altered based upon the monitored effect of various pacing settings of a patient's pacemaker on the ventricular pressure index. In altering the patient's pacing settings, the ventricular pressure index may be monitored on a periodic, continuous, or some other basis to retest the pacemaker settings to assure they are set optimally. For example, an A-V interval of a dual chamber pacemaker or of a cardiac resynchronization therapy can be adjusted to assure an optimal VPI. In a further example, the V-V interval of cardiac resynchronization therapy can be adjusted to ensure an optimal VPI.

The monitor of the ventricular pressure index may also be useful in initially setting or subsequently adjusting the settings of a drug delivery device or the like. For example, a pumping rate of a drug therapy pump may be adjusted to ensure an optimal VPI.

The monitoring of the ventricular pressure index of a heart failure patient for any of the above-described applications of the present invention can take place in either a system using an implantable medical device (IMD) or in a bedside monitoring medical device for use in a hospital setting.

Figure 2:
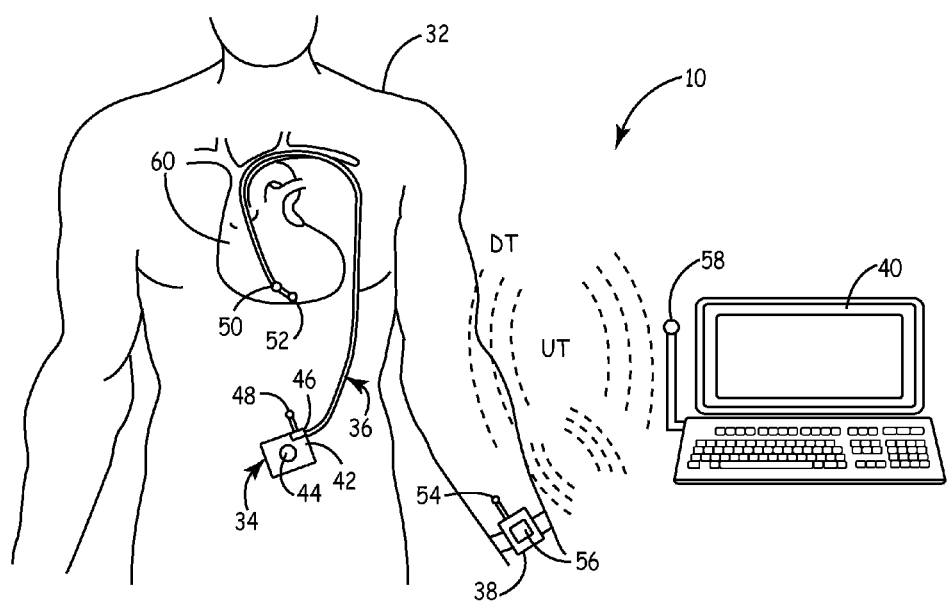
FIG. 2 is a diagram of a system for using an implantable medical device to monitor a heart failure patient for worsening heart failure.

FIG. 2 is a diagram of system 10 for using an IMD to monitor patient 32 for worsening heart failure. System 10 includes IMD 34, blood pressure sensor lead 36, atmospheric pressure reference monitor 38, and external computer 40. IMD 34 further includes hermetically-sealed housing 42, activity sensor 44, lead connector header 46, and telemetry antenna 48. Blood pressure sensor lead 36 includes blood pressure sensor 50 and electrogram (EGM) sense electrode 52. Atmospheric pressure reference monitor 38 includes telemetry antenna 54 and optional timepiece function 56. Computer 40 includes telemetry antenna 58.

In one embodiment, IMD 34 is the MEDTRONIC CHRONICLE implantable hemodynamic monitor (IHM) of the type described in commonly-assigned U.S. Pat. No. 5,368,040. IMD 34 is capable of storing data indicative of patient activity level as obtained from activity sensor 44. IMD 34 is further capable of storing blood pressure and heart rate data obtained from blood pressure sensor lead 36 connected to IMD 34 via lead connector header 46. Other possible configurations of the IMD 34 can provide cardioversion/defibrillation and/or pacing therapies requiring additional implantable cardiac leads and electrodes not shown in FIG. 2. IMD 34 may be implanted in the abdomen or upper chest of patient 32.

Blood pressure sensor lead 36 having multiple conductors locates blood pressure sensor 50 and EGM sense electrode 52 within the right ventricle of patient's heart 60. In one embodiment, blood pressure sensor lead 36 is a MEDTRONIC Model 4328A blood pressure sensor lead. In this embodiment, blood pressure sensor 50 is a pressure sensing transducer of the type disclosed in commonly-assigned U.S. Pat. No. 5,564,434. Blood pressure sensor lead 36 also incorporates a distal EGM sense electrode 52 and conventional soft pliant tines that provide passive fixation of sense electrode 52 into the ventricular apex in a manner well known in the art. The proximal connector assembly of blood pressure sensor lead 36 is configured in conformance with IS-1 standards for bipolar pacing leads and is fitted into a conforming bore of connector header 46 of IMD 34 in a conventional manner. The EGM of the heart, particularly the R-waves of the PQRST complex, is sensed between EGM sense electrode 26 and an indifferent electrode formed by hermetically-sealed housing 42 of IMD 34 in a conventional unipolar configuration.

Because the CHRONICLE Model 9520 IHM measures absolute blood pressure, patient 32 is also provided with atmospheric pressure reference monitor 38 to record atmospheric pressure values. In one embodiment, atmospheric pressure reference monitor 38 is a MEDTRONIC Model 2955HF atmospheric pressure reference monitor. Atmospheric pressure reference monitor 38 is schematically depicted as worn on the wrist of patient 32 with optional timepiece function 56, but it may take other portable configurations so that it can accompany patient 32 in her daily routine. The functions of an exemplary atmospheric pressure reference monitor 38 in relation to the IMD 14 and computer 38 are disclosed in commonly-assigned U.S. Pat. No. 5,904,708.

Computer 40 is used to communicate with IMD 34 and atmospheric pressure reference monitor 38 in order to program the operating modes and parameters of IMD 34 or interrogate the data stored in memory of the IMD 34 and atmospheric pressure reference monitor 38. Computer 40 can include a MEDTRONIC Model 9790 programmer or a PC with CHRONICLE software. Data accumulated by computer 40 is stored in a large FIFO buffer in RAM at a programmable resolution.

Uplink telemetry (UT) and downlink telemetry (DT) transmissions between telemetry antenna 48 of IMD 34 (schematically illustrated as extending from connector header 46 of IMD 34) and telemetry antenna 58 of computer 40 are schematically illustrated in FIG. 2. Similarly, UT and DT transmissions between an telemetry antenna 54 of the atmospheric pressure reference monitor 38 and telemetry antenna 58 of computer 40 are also illustrated in FIG. 2. A direct cable or plug-in connection can be made between ports of atmospheric pressure reference monitor 38 and computer 40 instead of employing the depicted UT and DT transmissions between telemetry antennas 54 and 58 when atmospheric pressure data is to be read from memory in atmospheric pressure reference monitor 38. In conventional use of system 10 depicted in FIG. 2, the storage of absolute blood pressure data and ambient pressure data continues for a period of days, and the data is periodically transmitted to computer 40 during a telemetry session initiated by medical personnel operating the external computer 40. In other embodiments, computer 40 may periodically initiate transfer of data itself. In still further embodiments, IMD 34 and atmospheric pressure reference monitor 38 may communicate with computer 40 in real-time. Computer 40 may also be a remote computer connected to IMD 34 via the Internet.

Figure 3:
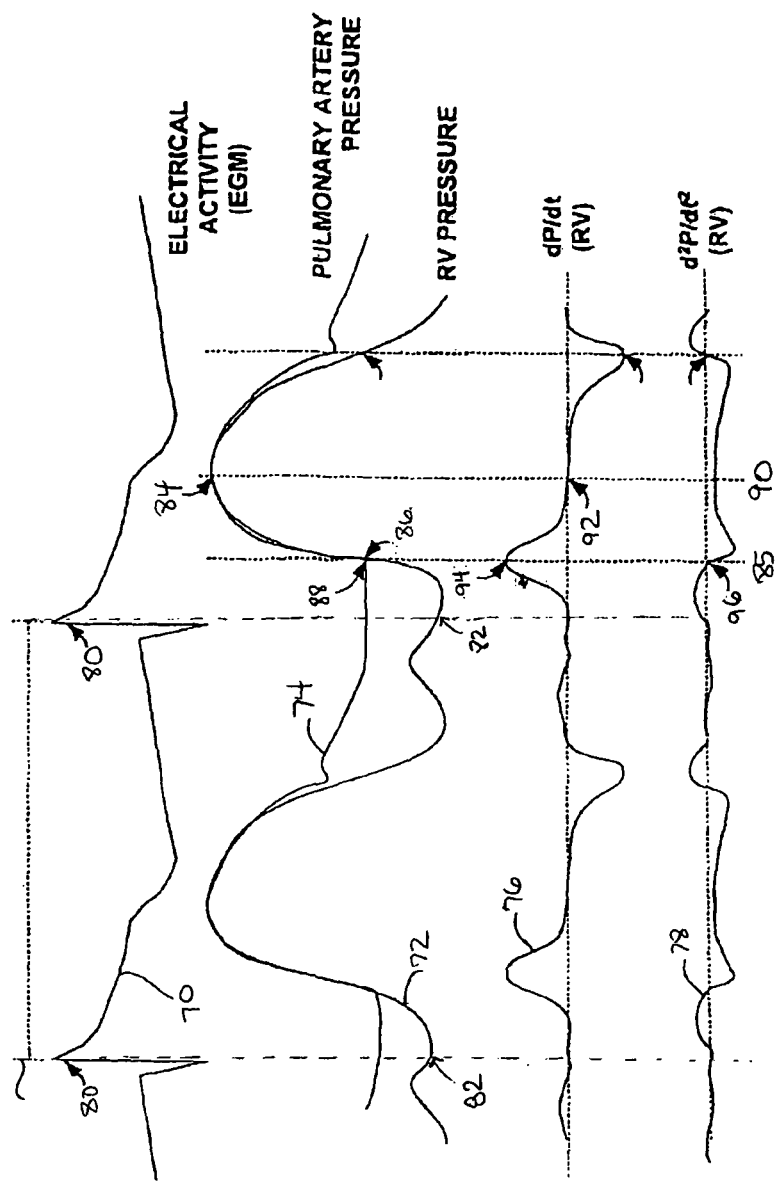
FIG. 3 is a timing diagram providing an overview of a mode of operation of an implantable medical device to determine a right ventricular pressure index for a heart failure patient.

FIG. 3 is a timing diagram providing an overview of a mode of operation of IMD 34 to determine right ventricular (RV) pressure index in accord with the present invention. FIG. 3 includes EGM signal 70 representative of the electrical activity in the right ventricle of the heart, RV pressure signal 72 representative of the fluid pressure in the right ventricle of the heart, and PA pressure signal 74 representative of the fluid pressure within the pulmonary arteries. FIG. 3 also includes first derivative dP/dt signal 76, and second derivative $d^2P/dt^2$ signal 78 derived by IMD 34 for the reasons described below.

R-wave 80 in EGM signal 70 represents ventricular depolarization of the heart, which is the start of ventricular contraction. Upon the occurrence of R-wave 80, pressure 72 in the right ventricle is at its minimum pressure 82, which is often referred to as the RV diastolic pressure. Following ventricular depolarization, pressure 72 in the right ventricle increases, eventually reaching its peak pressure 84, which is often referred to as the RV systolic pressure.

For a brief period at the start of ventricular contraction, no blood leaves the right ventricle, and the contraction is isovolumetric. During this isovolumetric contraction, the tricuspid valve at the entry of the right ventricle is closed by backward pressure differential forces. The pulmonary valve at the exit of the right ventricle is likewise closed, as pressure 72 in the right ventricle is insufficient to force blood through it. Consequently, this isovolumetric contraction causes the blood in the right ventricle to undergo increasing pressure 72. In a short time, pressure 72 in the right ventricle overcomes pressure 74 in the pulmonary arteries, drives the pulmonary valve open, and ejects blood from the right ventricle into the pulmonary arteries.

At time 85 when the pulmonary valve opens, pressure 74 within the pulmonary arteries is at its minimum pressure 86, which is often referred to as the PA diastolic pressure or PAD. Where a blood pressure sensor is not located in the pulmonary arteries, but only in the right ventricle, PA diastolic pressure 86 can be approximated from pressure 88 measured in the right ventricle at the time of the pulmonary valve opening. This value is often referred to as the estimated pulmonary artery diastolic pressure, or ePAD.

RV diastolic pressure 80 may be determined by a processor of IMD 34 as the first sample in RV pressure signal 72 after detection of R-wave 80 of EGM signal 70, or the value of RV pressure signal 72 at a start time of the ventricular contraction.

RV systolic pressure 84, which is the maximum pressure experienced in the right ventricle, may be identified by the processor of IMD 34 by applying a peak detection algorithm to RV pressure waveform 72. The processor may also determine RV systolic pressure 84 by locating the time of peak RV pressure 90 and finding the corresponding value on RV pressure waveform 72. Time of peak RV pressure 90 can be determined from dP/dt signal 76 as first zero-crossing 92 after the occurrence of R-wave 80 of EGM signal 70.

IMD 34 may identify ePAD 88 by processing RV pressure signal 72 to identify time of valve opening 85 and finding the corresponding value on RV pressure waveform 72. As described above, when the pressure in the right ventricle overcomes the pressure in the pulmonary arteries, the pulmonary valve is driven open. When the pulmonary valve opens, contraction is no longer isovolumetric. Pressure in the right ventricle, although still increasing due to ventricular contraction, increases at a slower rate. As a result, an inflection point in RV pressure signal 72 occurs at time of valve opening 85.

Because the slope of RV pressure signal 72 is at its maximum positive value at the inflection point, positive peak 94 of dP/dt signal 76 corresponds to the inflection point, or time of valve opening 85. The first time $d^2P/dt^2$ signal 78 goes negative (or first zero-crossing 96) after an occurrence of R-wave 80 will also correspond to time of valve opening 85. Thus, ePAD 88 may be determined by identifying the point on RV pressure signal 72 corresponding to either positive peak 94 of dP/dt signal 76 or to first zero-crossing 96 of $d^2P/dt^2$ signal 78.

In processing these signals, IMD 34 may differentiate RV pressure signal 72 to determine the first or second derivative of the pressure signal with respect to time. IMD 34 may further apply algorithms to detect the peaks and or zero-crossings of any of these signals or to identify the occurrence of R-wave 80 in the EGM signal 70.

Although shown operating in the right ventricle, the present invention is equally applicable to systems having sensors for measuring blood pressure within the left ventricle. Similar processing as identified above could determine the systolic and diastolic pressures in the left ventricle and to estimate the diastolic pressure in the aorta.

In addition to its application in an IMD, the present invention may also be incorporated in other medical hemodynamic monitoring devices, such as bedside monitoring systems which can simultaneously measure pressures in the right ventricle and the pulmonary arteries and or simultaneously measure pressures in the left ventricle and the aorta. In such system, it is not necessary to estimate pressures in the pulmonary arteries or the aorta. Of course, if the medical hemodynamic monitoring device does not include sensors for the blood vessels, pressures in the blood vessels can be estimated.

It is also contemplated that in a system having a blood pressure sensor located in a blood vessel rather than a ventricle, estimates of the pressures in the corresponding ventricle may be obtained from the blood vessel pressure signal.

EXAMPLE 1

Figure 4:
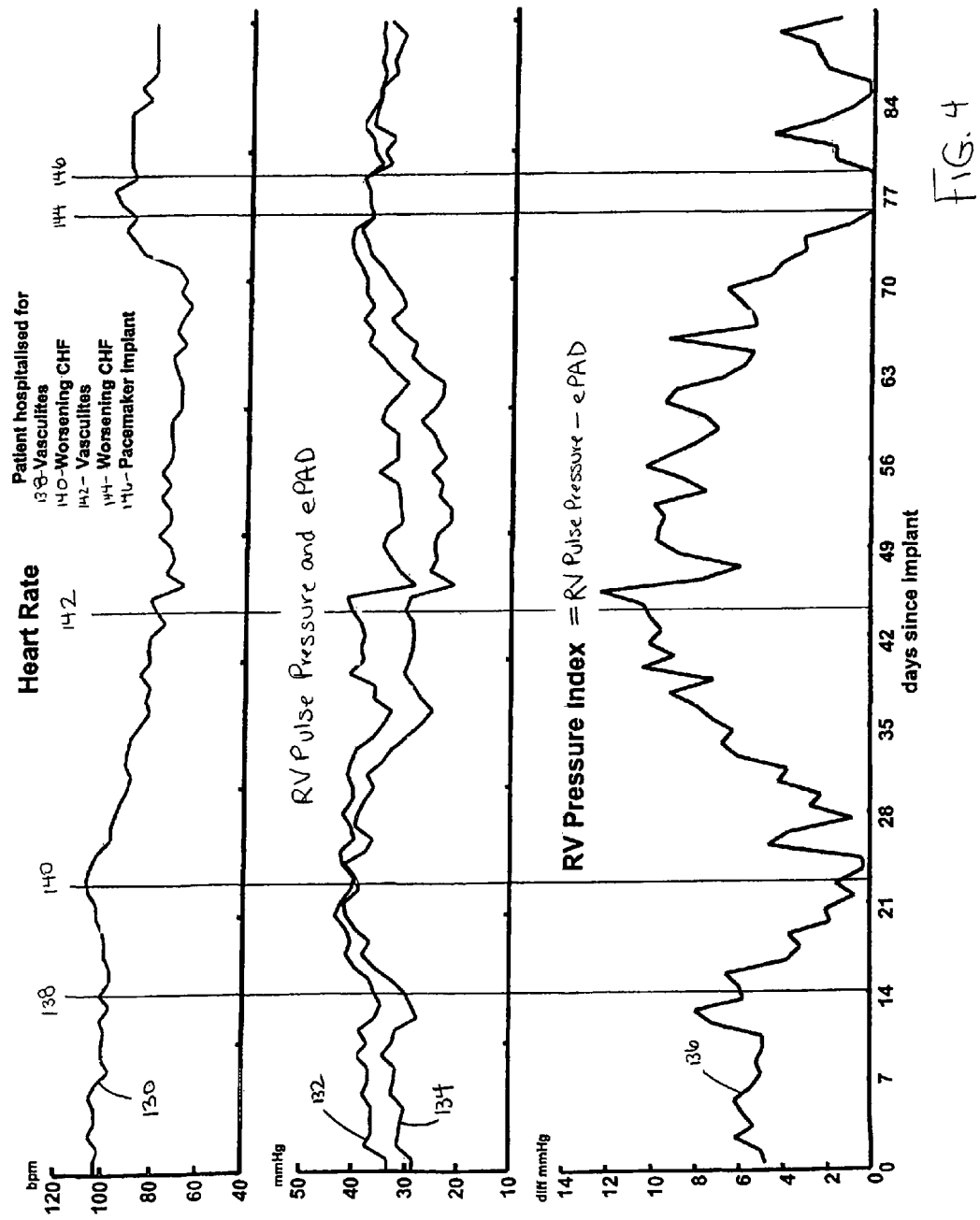
FIG. 4 is a graph illustrating the correspondence between a right ventricular pressure index in a patient and the patient's heart failure status over time.
Figure 5:
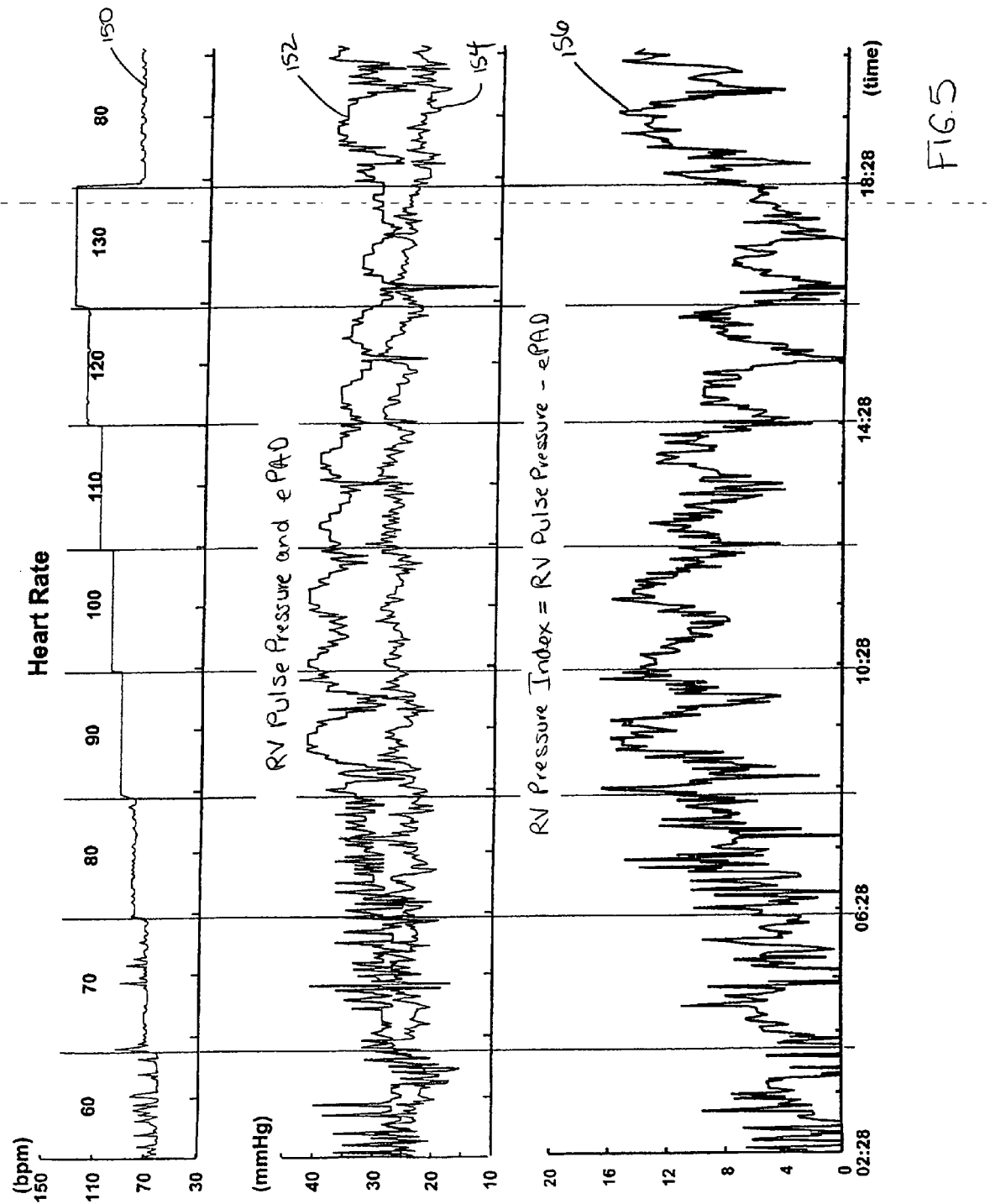
FIG. 5 is a graph illustrating an effect on a right ventricular pressure index in a patient as the patient is stepped through a plurality of pacing rates.

FIG. 4 is a graph illustrating the correspondence between the RV pressure index in a patient and the patient's heart failure status overtime. The patient was a sixty-seven year old male who had ideopathic cardiomyopathy diagnosed five years earlier. His past medical history included asthma and chronic heart failure. After two attempts of atrial cardioversions had failed, a CHRONICLE7 IHM was implanted in the patient. During the twelve months prior to implant, the patient was hospitalized three times for a total of twenty-three days.

The graph of FIG. 4 includes heart rate trend waveform 130, RV pulse pressure trend waveform 132, ePAD trend waveform 134, and RV pressure index trend waveform 136. Each waveform is plotted versus the number of days since the implant of the IHM. At time 138, which was fourteen days after the implant of the IHM, the patient was hospitalized in the dermatology department for vasculites on the lower legs. Nine days later, at time 140, the patient was transferred to the cardiology department with symptoms of worsening chronic heart failure and dyspnea. By about day thirty-five, the patient's chronic heart failure had stabilized, but the patient remained hospitalized. At time 142, about forty-four days from implant, the patient was transferred back to the dermatology department for increasing vasculites. About seventy days after the implant, the patient developed bradycardia with premature ventricular contractions (PVC) and ventricular tachycardia (VT), symptoms of more dyspnea and periods of severe cheyne-stokes respiration. At that time, the patient stopped receiving digitalis and CORDARONE. A few days later, at time 144, the patient was transferred back to the cardiology department. At time 146, a THERA SR VVI pacemaker was implanted into the patient. One day later, administration of digitalis was restarted, and another three days later, CORDARONE was restarted. The patient recovered well, but ninety-one days after implant of the IHM, the patient died.

In this example, the RV pressure index is a good indicator of worsening heart failure. The patient experienced worsening heart failure at times 140 and 144. Just prior to both of these times, RV pressure index trend waveform 136 decreased, thus signaling the onset of worsening heart failure. According to the data in FIG. 4, none of heart rate trend waveform 130, RV pulse pressure trend waveform 132, or ePAD trend waveform 134 alone signals the onset of this worsening heart failure.

EXAMPLE 2

The present invention may also be used in a method to determine a desired pacing rate for a patient having an implanted artificial pacemaker. In one example of this method, a patient underwent a test of several programmed heart rates twelve days after his artificial pacemaker was implanted. In the seven days leading up to this test, the patient's pacemaker was programmed to 80 bpm. After ten minutes of rest and heart rate of 80 bpm, the patient was paced at:
  60 bpm for 2 minutes;
  70 bpm for 2 minutes;
  80 bpm for 2 minutes;
  90 bpm for 2 minutes;
  100 bpm for 2 minutes;
  110 bpm for 2 minutes;
  120 bpm for 2 minutes;
  130 bpm for 2 minutes; and
  80 bpm for 2 minutes.

FIG. 6 is a graph illustrating heart rate trend waveform 150, RV pulse pressure trend waveform 152, ePAD trend waveform 154, and RV pressure trend index 156 over time as the patient steps through the above pacing schedule. The patient's physicians can monitor RV pressure index trend waveform 156 to avoid artificial heart rates that result in low RV pressure indices.

The present invention is based upon the discovery of a ventricular pressure index is a good predictor of worsening heart failure. Heart failure results in the deterioration of the above-described functioning of the heart. In particular, heart failure is the inability of the heart to efficiently pump blood to meet the demands of the body. As described below with respect to the pulmonary arteries, heart failure has dramatic effects on the pressures and volumes in the heart and its output blood vessels, which make the study of these cardiovascular data useful in diagnosing heart failure.

Pressure at any location in a compliant structure, such as the heart and blood vessels, is defined by the stiffness of the structure (which is the inverse of its compliance) and the volume in the structure. Over a range of volumes, the resultant pressures are defined by a compliance curve for that structure. Vascular structures have compliance relationships that tend to be generally linear over their normal physiological range of volumes and pressures, but nonlinear at the extreme volumes and pressures common with heart failure.

Looking at the pulmonary arteries, PA systolic pressure is typically dominated by the stroke volume (i.e., the quantity of blood pumped into the pulmonary arteries by the contraction of the right ventricle) and the stiffness of the pulmonary arteries into which a given stroke volume is ejected. In the pathological state of heart failure, where vascular volumes tend to be abnormally high, the system is working at the extreme, steeper portion of the pressure-volume relationship (i.e., the compliance curve). Thus, higher PA systolic pressures may result from the same or smaller stroke volumes than would result if the system were working at normal volumes. In extreme states, a very small stroke volume from the right ventricle ejected into the pulmonary artery can cause very large PA systolic pressures.

Diastolic pressure in the pulmonary arteries is predominately determined by the resistance in the pulmonary bed and the patient's heart rate, both of which tend to be quite elevated in heart failure patients. A quicker heart rate results in a shorter diastole period, which in turn provides less time for blood to flow out of the pulmonary artery before the next ejection, and thus less drop in PA pressure and a higher PA diastolic pressure. Increased pulmonary vascular resistance impedes blood flow from the pulmonary arteries during diastole, resulting in more blood in the structure at the end of diastole and therefore a higher PA diastolic pressure. This simple model of the flow dynamics in the pulmonary arteries may be complicated, as is well known, by other factors such as alveolar pressure.

An increase in PA systolic pressure will likely result in an increase in PA diastolic pressure. For instance, an increase in PA systolic pressure caused by a larger stroke volume will result in a higher PA diastolic pressure for the same diastolic period and vascular resistance. Depending on where the system is located on the pressure-volume curve, this effect can be more or less prominent. At high vascular volumes, factors that result in relatively small vascular volume changes can result in correspondingly large pressure changes.

Similarly, an increase in PA diastolic pressure will likely result in an increase in PA systolic pressure. If less blood flowed from the pulmonary arteries during a prior diastole B either because the diastolic time was less or because the pulmonary resistance was higher B then more blood is left in the pulmonary arteries when the next systole begins. Assuming the right heart has normal function and ejects an normal stroke volume, the next PA systolic pressure will be larger because the system will have moved up the pressure-volume curve.

The weighting of all the above factors is highly variable within a patient, and depends upon the patient's physiological status (i.e., the ability of the patient to respond normally to normal variations in hemodynamic factors) and pathological status (i.e., responses outside the normal range due to the presence of pathology).

The ventricular pressure index of the present invention was developed after studying these volumes and pressures in heart failure patients. The ventricular pressure index is based, in part, upon the hypothesis that heart failure patients with worsening heart failure status will be subject to an insult, either an unusual volume overload or a primary worsening of left ventricular function. This insult will cause a decrease in an ejection fraction of the left ventricle, thus resulting in a decrease in cardiac output. The decrease in cardiac output will result in an increase in volume in the right ventricle and pulmonary arteries. This increase in pulmonary volume may also directly or indirectly (through further activation of the sympathetic nervous system or circulating catecholamines or renin-angiotensin activation) further increase PA resistance. The heart rate may increase somewhat, shortening diastole. This combination of factors tends to result in a relatively large increase in PA diastolic pressure, a moderate increase in PA systolic pressure, and a significant but milder increase in RV diastolic pressure. The net result is a decrease in the relative difference in between PA diastolic pressure and RV pulse pressure.

In the case of a volume overload event, the kidneys tend to retain excess fluid volume, either in response to an increase in salt intake by the patient, worsening of kidney function, poor blood flow to the kidneys, or some combination of the above. This increased fluid volume acts to increase pressure in both the pulmonary blood vessels as well as in the veins leading to the right heart and the right heart itself. The higher pulmonary pressures may result in a further overload on the left ventricle, which might already be working at or near an overloaded state. This additional load on the left ventricle can result in a further reduction in the left ventricle output, and, to an additional increment, in pressures in the pulmonary blood vessels. Thus, an increase in pulmonary pressures, particular PA diastolic pressure, may be greater than the increase in RV pressure so that the ventricular pressure index shifts, indicating the worsened condition of the patient.

In sum, the present invention is a system and a method for predicting worsening heart failure. In particular, a pressure signal is sensed in a ventricle. From that pressure signal, a new ventricular pressure index equal to the ventricular pulse pressure minus the diastolic pressure in the corresponding output blood vessel is determined. When compared with a patient specific threshold, this ventricular pressure index serves to predict worsening heart failure and to further allow for automatic or physician-prescribed modification of the patient therapies to address the cause of the worsening disease.

Although the present invention has been described with reference to preferred embodiments, workers skilled in the art will recognize that changes may be made in form and detail without departing from the spirit and scope of the invention.

The invention claimed is:

1. A medical device for monitoring heart failure in a patient, the medical device comprising:
   an input circuit that receives a pressure signal representative of pressures sensed within a ventricle as a function of time; and
   a processor that derives from the pressure signal a ventricular pressure index for a ventricular contraction based upon pressures in the ventricle and provides an output based upon the ventricular pressure index, wherein said ventricular pressure index corresponds to one of: a heart failure status or a changing heart failure status;
   wherein, for the ventricular contraction, the processor determines from the pressure signal a diastolic pressure in the ventricle and a systolic pressure in the ventricle and a diastolic pressure in a vessel into which the ventricle pumps blood; and
   wherein the processor determines the ventricular pressure index for a ventricular contraction as a function of the systolic pressure in the ventricle, the diastolic pressure in the ventricle, and the diastolic pressure in the blood vessel.

2. The medical device of claim 1 and further comprising a blood pressure sensor locatable in the ventricle for providing the pressure signal to the input circuit.

3. The medical device of claim 1 and further comprising memory for storing a ventricular pressure index threshold determined for the patient during an initialization period, wherein the processor detects when the ventricular pressure index has fallen below the ventricular pressure index threshold.

4. The medical device of claim 3 wherein an output provided by the processor comprises a warning signal indicating that the ventricular pressure index has fallen below the ventricular pressure index threshold.

5. The medical device of claim 1 wherein the output provided by the processor is a therapy control signal based upon the ventricular pressure index, the control signal being provided to adjust a therapy of the patient.

6. The medical device of claim 1 wherein the output is a waveform representing the ventricular pressure index as a function of time.

7. A method for predicting worsening heart failure, the method comprising:
   for a ventricular contraction, sensing blood pressures within a ventricle of a patient's heart as a function of time;
   deriving from the sensed blood pressures a ventricular pressure index based upon blood pressures in the ventricle; and
   providing an output based upon the ventricular pressure index, wherein said ventricular pressure index corresponds to one of: a heart failure status or a changing heart failure status, and further comprising;
   determining from the sensed blood pressures a diastolic pressure in the ventricle and a systolic pressure in the ventricle; and
a diastolic pressure in a blood vessel into which the ventricle pumps blood; and
   wherein determining a ventricular pressure index comprises determining the ventricular pressure index as a function of the systolic pressure in the ventricle, the diastolic pressure in the ventricle, and the diastolic pressure in the blood vessel.

8. The method of claim 7 wherein the blood pressure is sensed by a blood pressure sensor located in the ventricle of the heart.

9. The method of claim 8 wherein the ventricle is a right ventricle.

10. The method of claim 7 and further comprising:
    determining a ventricular pressure index threshold for the patient during an initialization period; and
    detecting when the ventricular pressure index has fallen below the ventricular pressure index threshold.

11. The method of claim 10 wherein providing an output based upon the ventricular pressure index comprises:
    providing a warning upon the detection of the ventricular pressure index falling below the ventricular pressure index threshold.

12. The method of claim 7 wherein providing an output based upon the ventricular pressure index comprises:
    providing a therapy control signal based upon the ventricular pressure index, the control signal being provided to adjust a therapy of the patient.

13. The method of claim 7 wherein providing an output based upon the ventricular pressure index comprises:
    outputting a waveform representing the ventricular pressure index as a function of time.

14. A method for predicting worsening heart failure in a patient, the method comprising:
    sensing blood pressures within a patient as a function of time;
    determining from the sensed blood pressures a diastolic pressure in a ventricle of the patient's heart, a systolic pressure in the ventricle and a diastolic pressure in a blood vessel into which the ventricle pumps blood; and deriving from the sensed blood pressures a ventricular pressure index corresponding to one of: a heart failure status or a changing heart failure status, the ventricular pressure index based upon the systolic pressure in the ventricle, the diastolic pressure in the ventricle, and the diastolic pressure in the blood vessel; and providing an output based upon the derived ventricular pressure index.

15. The method of claim 14 wherein sensing blood pressures comprises sensing blood pressures using a sensor placed in the patient's ventricle.

16. The method of claim 14 wherein sensing blood pressures comprises sensing blood pressures using a sensor located in the blood vessel into which the ventricle pumps blood.

17. The method of claim 14 further comprising:
determining a ventricular pressure index threshold for the patient during an initialization period; and
detecting when the ventricular pressure index has fallen below the ventricular pressure index threshold.

18. The method of claim 17 wherein providing an output based upon the ventricular pressure index comprises:
providing a warning upon the detection of the ventricular pressure index falling below the ventricular pressure index threshold.

19. The method of claim 14 wherein:
providing an output based upon the ventricular pressure index comprises providing a therapy control signal based upon the ventricular pressure index; and
the method further comprises employing the control signal to adjust a therapy provided to the patient.

* * * * *